United States Patent [19]
Ohsuga et al.

[11] Patent Number: 5,831,037
[45] Date of Patent: Nov. 3, 1998

[54] METHOD FOR CLINICAL EXAMINATION BASED ON THE STRUCTURES OF IMMUNOGLOBIN G-LINKED OLIGOSACCHARIDES

[75] Inventors: Hiroyuki Ohsuga, Handa; Hiroaki Nakagawa, Nagoya; Chizu Ishida, Kasugai; Masahiro Fujimori; Yoshinori Tsukamoto, both of Handa; Noriko Takahashi, Nagoya; Yoshiya Kawamura, Kounan; Masashi Mizokami, Chiryu; Koichi Sato, Nagoya; Kazuo Yoshioka, Kawachinagano; Tetsuya Kibe, Nagoya, all of Japan

[73] Assignee: Nakano Vinegar Co., Ltd., Handa, Japan

[21] Appl. No.: 501,761

[22] Filed: Jul. 12, 1995

[30] Foreign Application Priority Data

Jul. 14, 1994 [JP] Japan .................................. 6-162530
May 17, 1995 [JP] Japan .................................. 7-118769

[51] Int. Cl.[6] .................................................. G01N 33/48
[52] U.S. Cl. ............................ 530/413; 436/87; 436/94; 436/161; 436/177; 436/509; 436/824
[58] Field of Search ............................. 436/87, 94, 161, 436/177, 509, 824; 530/413

[56] References Cited

U.S. PATENT DOCUMENTS

| | | | |
|---|---|---|---|
| 5,205,917 | 4/1993 | Klock, Jr. ............................ | 204/182.5 |
| 5,468,620 | 11/1995 | Molloy et al. ......................... | 435/7.1 |
| 5,472,582 | 12/1995 | Jackson ............................... | 204/180.1 |

FOREIGN PATENT DOCUMENTS

| | | |
|---|---|---|
| 0 189 388 | 7/1986 | European Pat. Off. . |
| 0398292 | 11/1990 | European Pat. Off. . |

OTHER PUBLICATIONS

Kobata, Glycobiology, 1, 5–8, 1990.
Biochemistry, vol. 26, "Comparative Structural Study of the N–Linked Oligosaccharides of Human Normal and Pathological Immunoglobulin in G", Noriko Takahashi, et al. 1987, pp. 1137–1144.
Jour. Exp. Med., vol. 167, "Age–Related Galactosylation of the N–linked Oligosaccharides of Human Serum IgG", Thomas Rademacher, et al. May 1988, pp. 1731–1736.
Biochemical and Biophysical Research Communications, vol. 85, "Structure Analyses of Oligosaccharides by Tagging of the Reducing End Sugars with a Fluorescent Compound", Sumihiro Hase, et al. Nov. 14, 1978, pp. 257–263.
Agric. Biol. Chem., vol. 54, "Improved Method for Fluorescence Labeling of Sugar Chains with Sialic Acid Residues", Akihiro Kondo, et al. 1990, pp. 2169–2170.
Biochemistry and Molecular Biology International, vol. 32, No. 5, pp. 897–902, Apr. 1994, A. Kondo, et al., "Analysis of Oligosaccharides of Human IgG from Serum of Leukemia Patients".

*Primary Examiner*—David Saunders
*Attorney, Agent, or Firm*—Oblon, Spivak, McClelland, Maier & Neustadt, P.C.

[57] ABSTRACT

The present invention relates to a novel clinical examination method which comprises analyzing the alteration in the amount of a specific component in oligosaccharides of immunogloblin G. Human diseases such as liver diseases, malignant hypertension, immunogloblin A-nephropathy, pediatric disorders, etc., are examined in terms of the alteration in bisecting N-acetylglucosamine-containing oligosaccharides in immunogloblin G from collected humor. The present invention provides highly accurate information in a manner applicable to practical operation for examination of liver diseases, allergic diseases, malignant hypertension, immunogloblin A nephropathy, pediatric disorders, as well as aging-dependent variations and the therapeutic effect of interferon.

6 Claims, 12 Drawing Sheets

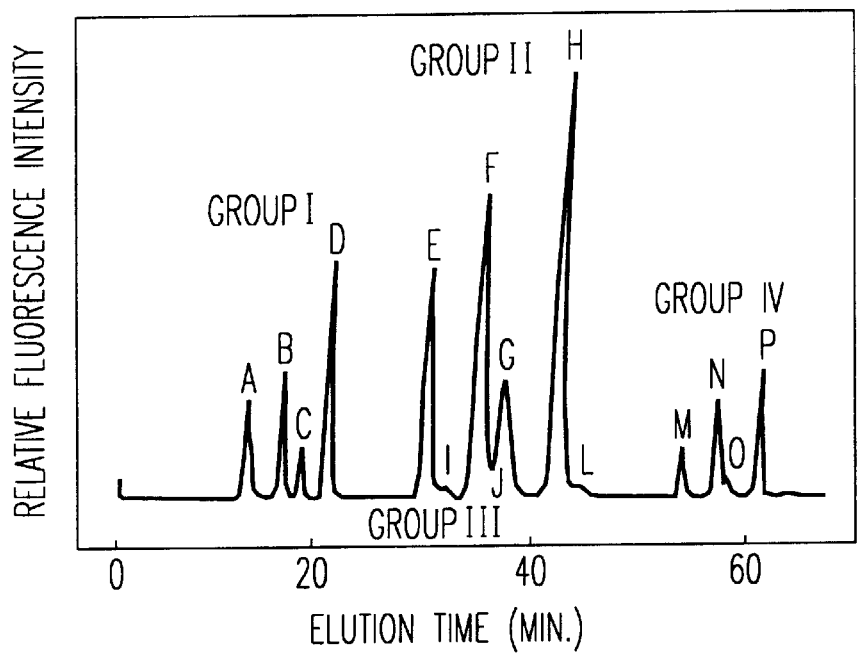
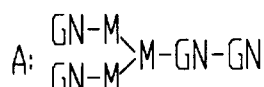 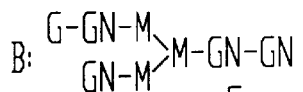 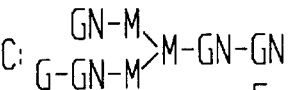
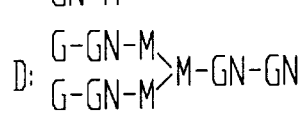 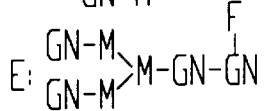 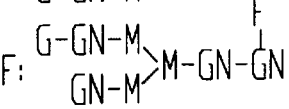
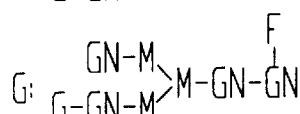 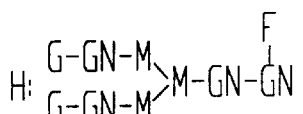 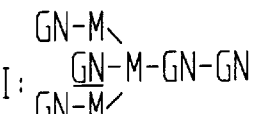
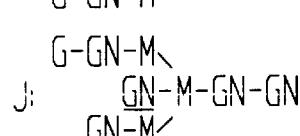 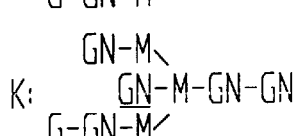 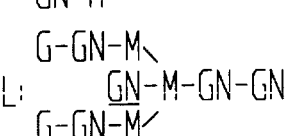
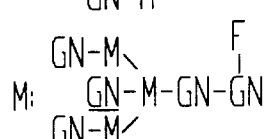 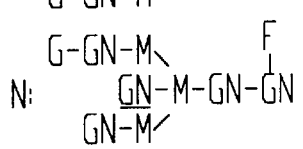 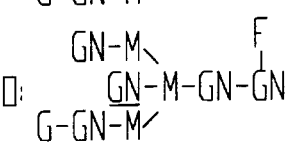
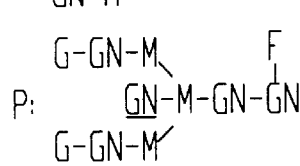  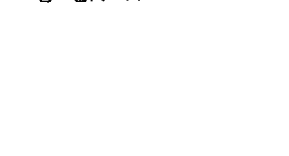
G: GALACTOSE, M: MANNOSE, F: FUCOSE, GN: N-ACETYLGLUCOSAMINE,
GN: BISECTING N-ACETYLGLUCOSAMINE.
*FIG. 1*

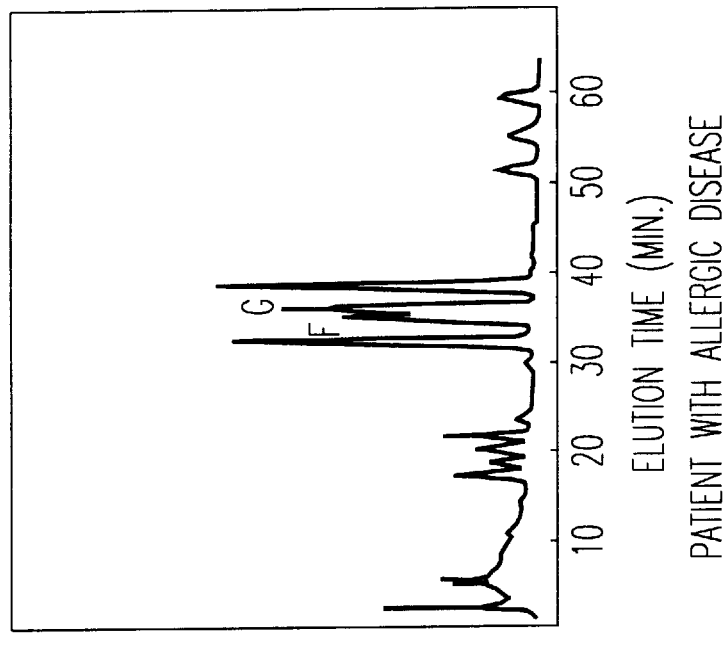
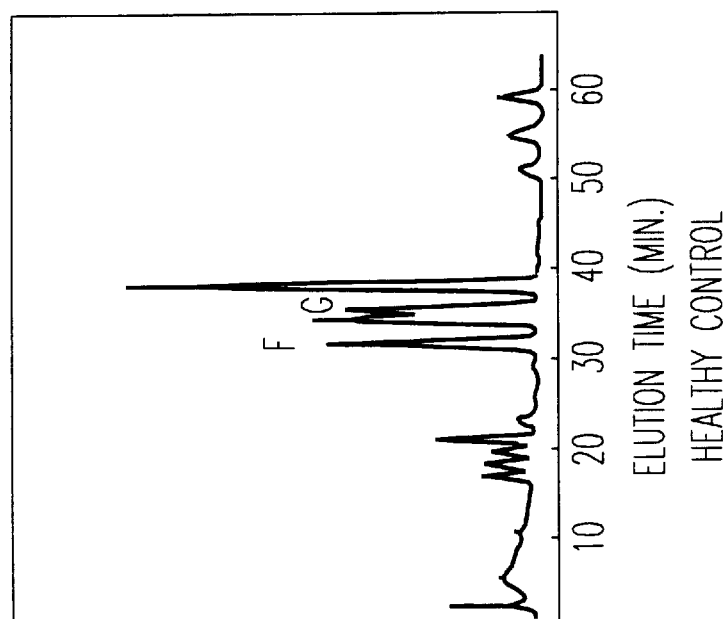

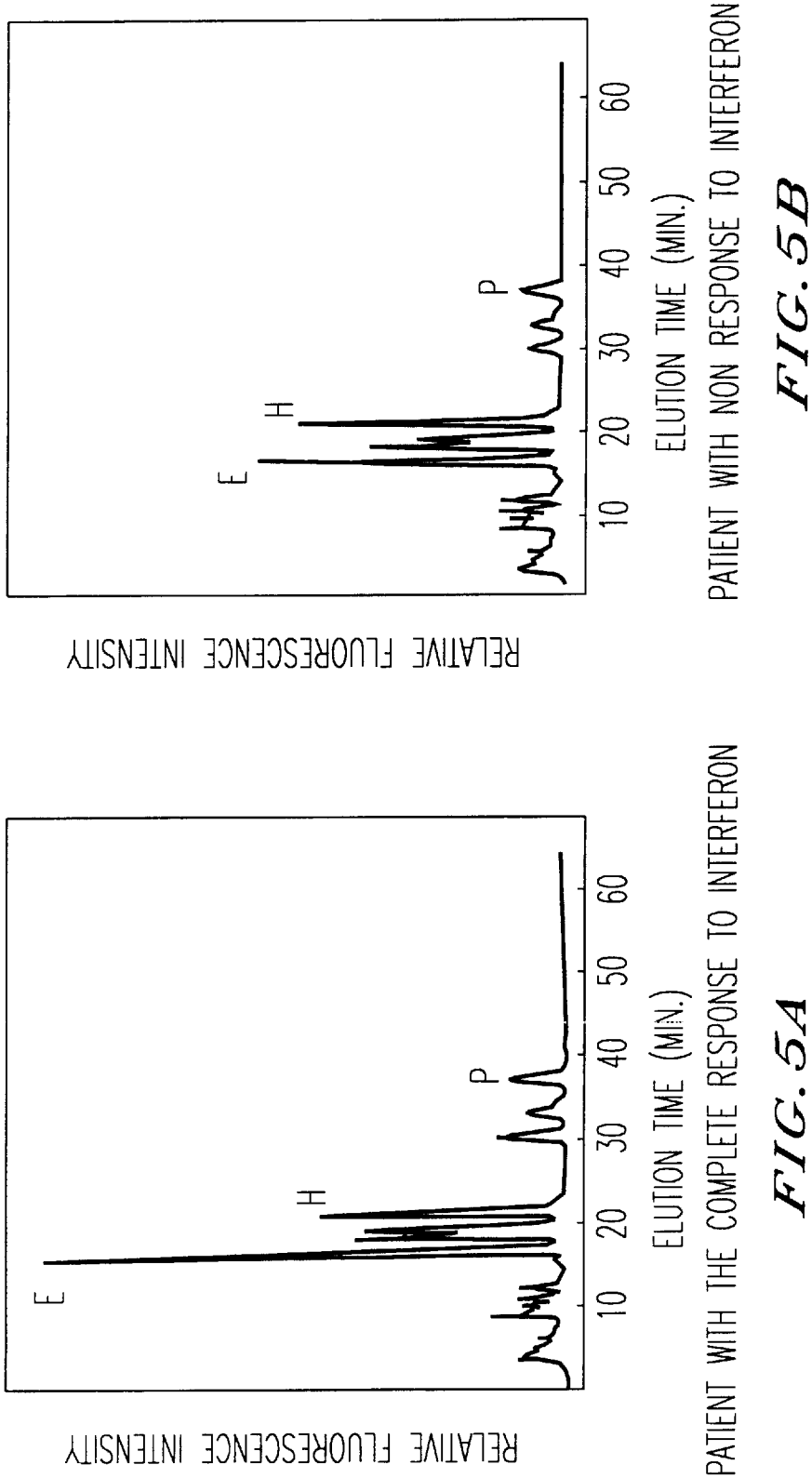

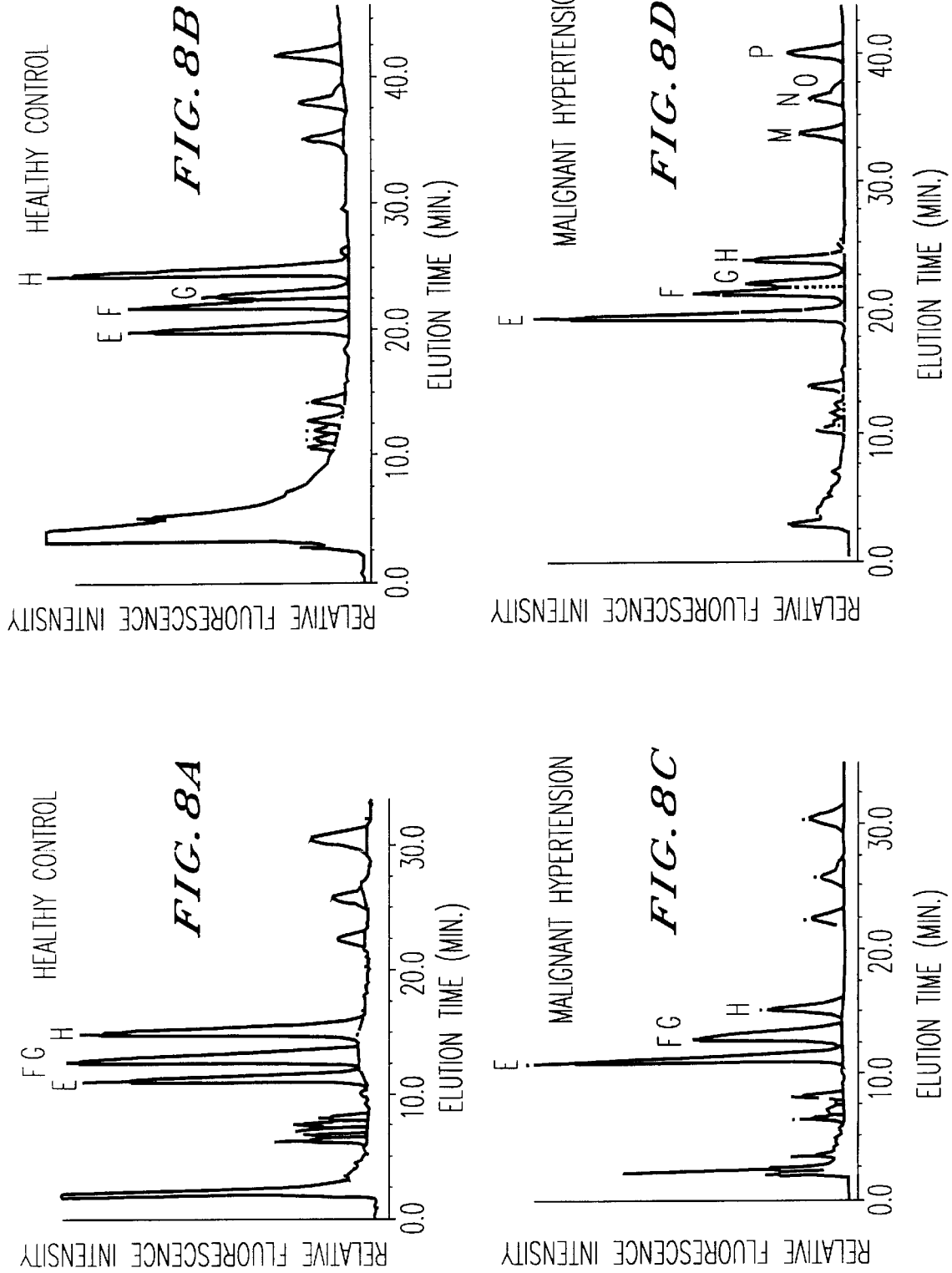

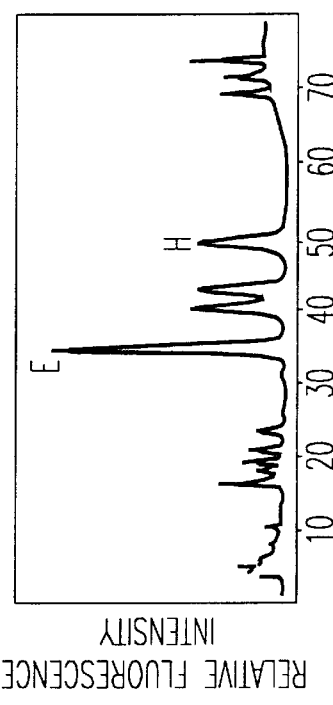
FIG. 12A (1) NEURODEGENERATIVE DISORDER(S) OF UNKNOWN CAUSES
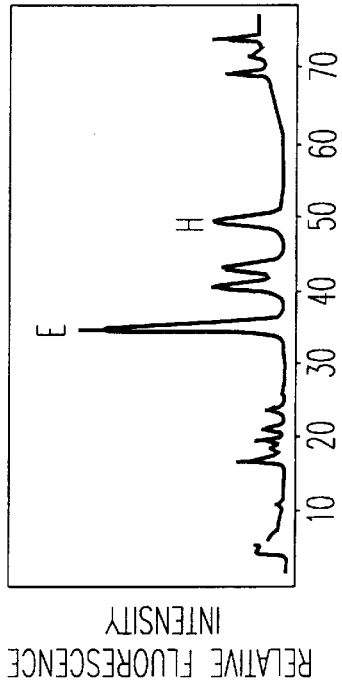
FIG. 12B (2) GAUCHER'S DISEASE
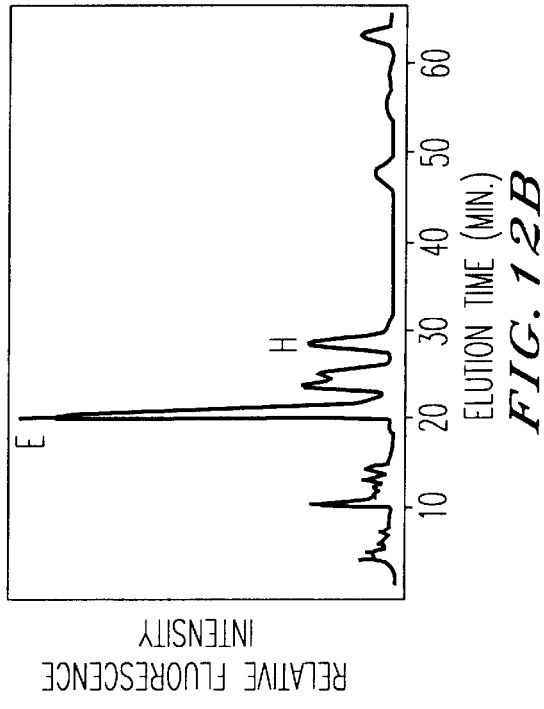
FIG. 12C (3) TAKAYASU SYNDROME
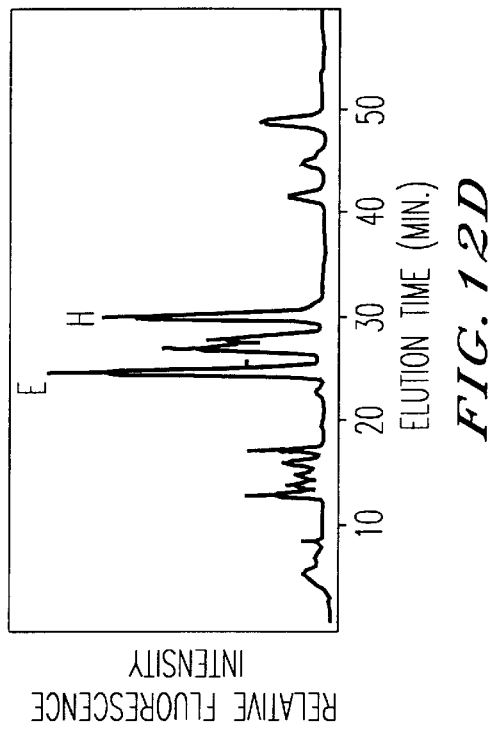
FIG. 12D (4) DOWN'S SYNDROME

METHOD FOR CLINICAL EXAMINATION BASED ON THE STRUCTURES OF IMMUNOGLOBIN G-LINKED OLIGOSACCHARIDES

FIELD OF THE INVENTION

The present invention relates to a method for clinical examination of disease which comprises examining the alteration in the amount of oligosaccharides linked to glycoprotein immunogloblin G in tissue or humor.

BACKGROUND OF THE INVENTION

The importance of information on oligosaccharide-containing living materials has come to draw attention with increasing biochemical and medical knowledge in recent years, and the examination of the alteration in the amount of trace oligosaccharides is attempted for some living materials such as lectin, antibody, etc. However, these examinations present disadvantages such as poor quantification and difficult detection of the alteration in a trace amount, and furthermore, glycoproteins (e.g. alpha fetoprotein and chorionic gonadotropin), i.e. a group of oligosaccharide-containing living materials known to undergo alterations with the progress of diseases, are hard to obtain from patients in an amount enough for analysis in methods of high quantification. If the alteration in the amount of a specific kind of oligosaccharide is assumed attributable to the disease in question and it is therefore expected that the disease can be clinically examined by analysis of the oligosaccharide, it is difficult to purify a sample from a patient and analyze it in detail for the oligosaccharide. Under such circumstances, the present inventors have extensively studied the clinical application of oligosaccharides of immunogloblin G (IgG) i.e. the most abundant glycoprotein in serum, and they have arrived at an epoch-making invention which permits the relative amount of each IgG oligosaccharide to be determined in detail without any further burden on the patient with several hundred microliters of serum as the remainder of blood collected for use in the conventional clinical examination.

Immunocompetent cells in the living system are classified roughly into monocytes/macrophages, T lymphocytes and B lymphocytes. The surface of their cell membrane carries antigen-binding receptors with antigenic specificity to a wide variety of antigens. In particular, B lymphocytes produce 5 classes of immunogloblin (M, G, A, E, and D) to remove the antigens effectively.

About half the glycoproteins in serum are immunogloblins, of which IgG accounts for about 80% of the total immunogloblins. IgG has a molecular weight of 150,000 with 1.4% carbohydrate, each molecule containing two oligosaccharides. Oligosaccharides of IgG are bound to Fc domains in the immunogloblin molecule. In the case of normal serum, the relative amount of each oligosaccharide in IgG is always constant, and 16 or more oligosaccharide structures have been found in asialo oligosaccharides. In a previous report, the present inventors could isolate all 16 kinds of oligosaccharides from IgG to almost homogeneity in only one step by high performance liquid chromatography (HPLC) on an ODS-silica column (Takahashi et al., Biochemistry, 26, 1137–1144 (1987)).

In human IgG, there are 16 classes of oligosaccharides A–P, and their elution pattern is as shown in FIG. 1 ("Seibutukagaku Jikkenho" (Experimental Methods in Biological Chemistry), Method for Study of oligosaccharides of Glycoprotein, vol. 23, p. 144, published by Gakkai Shuppan Center (1989) and compiled by Noriko Takahashi; and Takahashi et al., Biochemistry, 26, 1137–1144 (1987)). On the basis of this pattern, the oligosaccharides of IgG can be divided into the following 4 groups:

(1) a complex type oligosaccharide group not containing fucose α1→6 bond or bisecting N-acetylglucosamine [group I (A, B, C, D)];

(2) a complex type oligosaccharide group containing fucose α1→6 bond [group II (E, F, G, H)];

(3) a complex type oligosaccharide group not containing fucose α1→6 bond but containing bisecting N-acetylglucosamine [group III (I, J, L)]; and (4) a complex type oligosaccharide group containing fucose α1→6 bond and bisecting N-acetylglucosamine [group IV (M, N, O, P)].

Each of these groups further contains an oligosaccharide containing 0, 1 or 2 galactose molecules, the proportion of each group being roughly constant in normal serum IgG. The relative amount of each oligosaccharide of IgG is always constant in the case of healthy persons.

In the case of patients, however, the relative amount of each oligosaccharide of IgG varies with changes in environment in and around cells, resulting in an alteration in an elution pattern of oligosaccharides in reverse phase column chromatography. Hence, the examination of various diseases will be feasible effectively by quantitative analysis of elution patterns of oligosaccharides of IgG from patients with the diseases. From a practical point of view, however, the examination or grouping of certain diseases in terms of the amount of a single oligosaccharide of IgG often leads to inaccurate evaluation. The present inventors found that diseases can be grouped in terms of the relative amounts of two or more oligosaccharides of IgG by use of the areas of their corresponding peaks in HPLC. This method can be clinically used for more accurate diagnosis of diseases.

Unlike the protein, the oligosaccharide is highly related to various diseases since it is controlled not only by the gene but also by environment around cells. For example, it is known that a significant alteration occurs in the relative amounts of the oligosaccharides of IgG from patients with e.g. rheumatoid arthritis and a significant alteration occurs further in the content of galactose in the oligosaccharides.

Hepatitis is one of the major human diseases at present. In particular, C-type hepatitis is caused by infection via a transfusion and proceeds from chronic hepatitis through liver cirrhosis to hepatocellular carcinoma.

Although extensive studies have been made on clinical examination and diagnosis of hepatitis by conventional biochemical means, diagnostic accuracy is still not so high ranging from 60–70% to 30–50%. For this reason, the diagnosis of this disease has been made in combination with other methods, but accurate information on extremely complicated pathological changes in the living system is hard to obtain. Hence, it has become an emergent and extremely important task to develop highly accurate examination methods.

Interferon attracts attention as the only agent for treatment of hepatitis of both B and C types. However, patients with the complete response to interferon are about 30% of the whole patients with hepatitis and there are a large number of patients with non response to interferon regardless of enormously high costs for treatment. Hence, if it can be predicted before treatment with interferon whether the complete response to interferon can be brought about or not, this will be essential for selection of treatment.

Under the present situation where medical technology has greatly been advanced, an increase in old population has become a social issue. If it is elucidated how in vivo oligosaccharides are altered with aging, they not only serve as an indicator of aging but also can foretell whether the cause and progress of disease is caused by another disease or by a decrease in immunity with aging, and the analysis of aging will be useful particularly in the health control of the old.

Allergic disease such as pollinosis, atopic dermatitis, etc., resulting from such factors as modern diverse eating habits, plant pollen, stress, etc., has become a major problem. Allergic disease is assumed to be an abnormality of the immunoreaction system. Oligosaccharides of IgG are essential in the immune system for the transmission of a series of information such as complement activity, and if an alteration in their structure is caused by the influence of allergic disease, such alteration can be used for the diagnosis of allergic disease.

Hypertension is a principal factor of other diseases in the circulatory system including cardiac disease and apoplexy. The number of patients with hypertension increases with increasing old population. It is estimated that the numbers of hospitalized patients and outpatients with hypertension have increased about 5 and 4 times respectively in the last 30 years. Malignant Hypertension is a disease with highly elevated diastolic blood pressure (over 140 mmHg) and hypertensive retinopathy (Keith-Wagener III or IV), and it may occur in both primary and secondary hypertension. Diagnosis of the disease is made by blood pressure and retinal examination. The condition of disease is grasped by examinations of cardiac and vascular progress from the disease. Renal function tests which include chemical examination on serum creatinine and urinalysis are important among them. Basically measurement of outpatient casual blood pressure is used for diagnosis, and sphygmomanometry for 24 hours is preferred if possible. But usually it is hard to examine all of the condition including blood pressure during sleep and in activity.

Immunogloblin A nephropathy (referred to hereinafter as "IgA nephropathy") is one kind of glomerular disease by which IgA and complement C3 are specifically deposited on the kidney. It was found that IgG is also deposited in a relatively large amount in IgA nephropathy. Although urinalysis and histologic examination are known for diagnosis of IgA nephropathy, urinalysis presents drawbacks including the inconvenient collection of urine and the difficult application of stored urine to e.g. urine sediments, while histologic examination such as renal biopsy gives a pain and burden on patients.

Unlike adult diseases, pediatric disorders include a large number of diseases, the causes of which have still not been elucidated, and there are further diseases occurring exclusively in infants. Hence, a large number of diseases named "syndrome" are included in pediatric disorders. The diagnosis of pediatric disorders is carried out conventionally using blood examination, urinalysis or image diagnosis in combination with examination of outward symptom. In many cases, however, it is difficult to find appropriate examination and treatment of the disorders.

SUMMARY OF THE INVENTION

Under such circumstances, the object of the present invention is to provide novel methods for clinical examination by analyzing the alteration in the amount of a specific component in oligosaccharides of IgG.

The present invention is a method for examination of human diseases, which comprises analyzing the alteration in the amount of bisecting N-acetylglucosamine-containing oligosaccharides of IgG in collected humor.

Further, the present invention is a method for examination of human disease, which comprises analyzing the alterations in the amounts of both bisecting N-acetylglucosamine-containing oligosaccharides and galactose-containing oligosaccharides of IgG in collected humor.

Further, the present invention is a method for examination of human disease, which comprises purifying IgG from collected humor, separating and labeling oligosaccharides from the purified IgG, and subjecting the oligosaccharide fraction to high performance liquid chromatography on a reverse phase chromatography column to analyze the alteration in the amount of bisecting N-acetylglucosamine-containing oligosaccharides of IgG.

Further, the present invention is a method for examination of human disease, which comprises purifying IgG from collected humor, separating and labeling oligosaccharides from the purified IgG, and subjecting the oligosaccharide fraction to high performance liquid chromatography on a reverse phase chromatography column to analyze the alterations in the amounts of both bisecting N-acetylglucosamine-containing oligosaccharides and galactose-containing oligosaccharides of IgG.

Further, the present invention is the method for examination of human disease, in which the human disease is liver diseases, malignant hypertension, immunogloblin A nephropathy or pediatric disorders.

Further, the present invention is a method for examination of aging-dependent variations, which comprises analyzing the alteration in the amount of galactose-containing oligosaccharides and/or bisecting N-acetylglucosamine-containing oligosaccharides of IgG in collected humor.

Further, the present invention is a method for examination of allergic disease, which comprises analyzing the ratio in the amounts between two kinds of fucosyl monogalactosyl oligosaccharides with galactose linked directly to a non-reducing terminal N-acetylglucosamine.

Further, the present invention is a method for examination of allergic disease, which comprises purifying IgG from collected humor, separating and labeling oligosaccharides from the purified IgG, and subjecting the oligosaccharide fraction to high performance liquid chromatography on a reverse phase chromatography column to analyze the ratio in the amounts between two kinds of fucosyl monogalactosyl oligosaccharides with galactose linked directly to a non-reducing terminal N-acetylglucosamine.

Further, the present invention is a method for examination of the therapeutic effect of interferon, which comprises analyzing the alteration in the amount of galactose-containing oligosaccharides of IgG in collected humor.

Further, the present invention is a method for examination of the therapeutic effect of interferon, which comprises purifying IgG from collected humor, separating and labeling oligosaccharides from the purified IgG, and subjecting the oligosaccharide fraction to high performance liquid chromatography on a reverse phase chromatography column to analyze the alteration in the amount of galactose-containing oligosaccharides of IgG.

Further, the present invention is a method for examination of human diseases, aging-dependent variations, allergic diseases and the therapeutic effect of interferon, in which the reverse phase chromatography column is an OD column.

The "bisecting N-acetylglucosamine" referred to in the present invention is N-acetylglucosamine linked to β-mannose via 1→4 bond as shown in I, J, K, L, M, N, O and P among 16 kinds of oligosaccharides of human IgG (in FIG. 1, N-acetylglucosamine is designated GN.). The "two kinds of fucosyl monogalactosyl oligosaccharides with galactose linked directly to a non-reducing terminal N-acetylglucosamine" correspond to F and G among oligosaccharides of IgG (see FIG. 1).

As the collected humor in the present invention, mention may be made of blood, semen, cerebrospinal fluid, amniotic fluid, lymph, etc.

BRIEF DESCRIPTION OF THE DRAWINGS

FIG. 1 shows an elution pattern of IgG oligosaccharides labeled with 2-aminopyridine from an QDS silica column, along with the corresponding structures of oligosaccharides.

FIG. 4 shows elution patterns of the oligosaccharides of IgG from a healthy control (FIG. 4A) and a patient (FIG. 4B) with allergic disease from an ODS-silica column. "F" and "G" are the designations of peaks.

FIG. 5 shows an elution pattern from an ODS-silica column where the samples applied are the oligosaccharides of IgG from a patient with chronic C-type hepatitis who experienced the complete response to interferon (FIG. 5A) or non response (FIG. 5B). "E", "H" and "P" are the designations of peaks.

FIGS. 8A–8D show elution patterns from ODP column and ODS-silica column where the samples applied were the oligosaccharides of IgG from the healthy control and a patient with malignant hypertension. An elution pattern of oligosaccharides of IgG from one patient out of 3 examined patients with malignant hypertension is shown. "E", "F", "G", "H", "M", "N", "O" and "P" are the designations of peaks.

Alteration in the amount of galactose-containing oligosaccharides=peak H/peak E.

Alteration of in the amount of bisecting N-acetylglucosamine-containing oligosaccharides=total area of peaks M–P/total area of peaks E–H. The designations of peaks follow the designations of peaks in FIG. 8.

Figure 10:
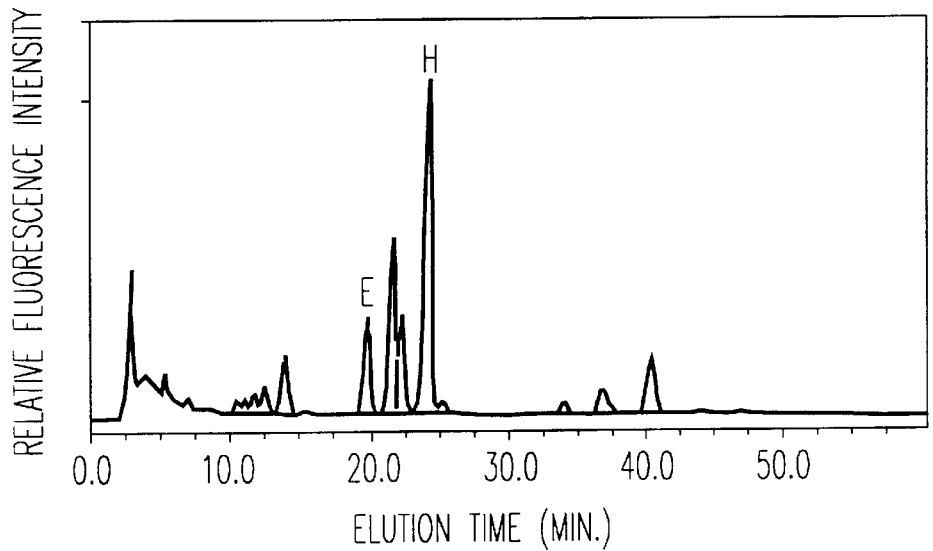

FIG. 10 shows an elution pattern from an ODS-silica column where the sample applied was oligosaccharides of IgG from a patient with IgA nephropathy. "E" and "H" are the designations of peaks.

Figure 11B:
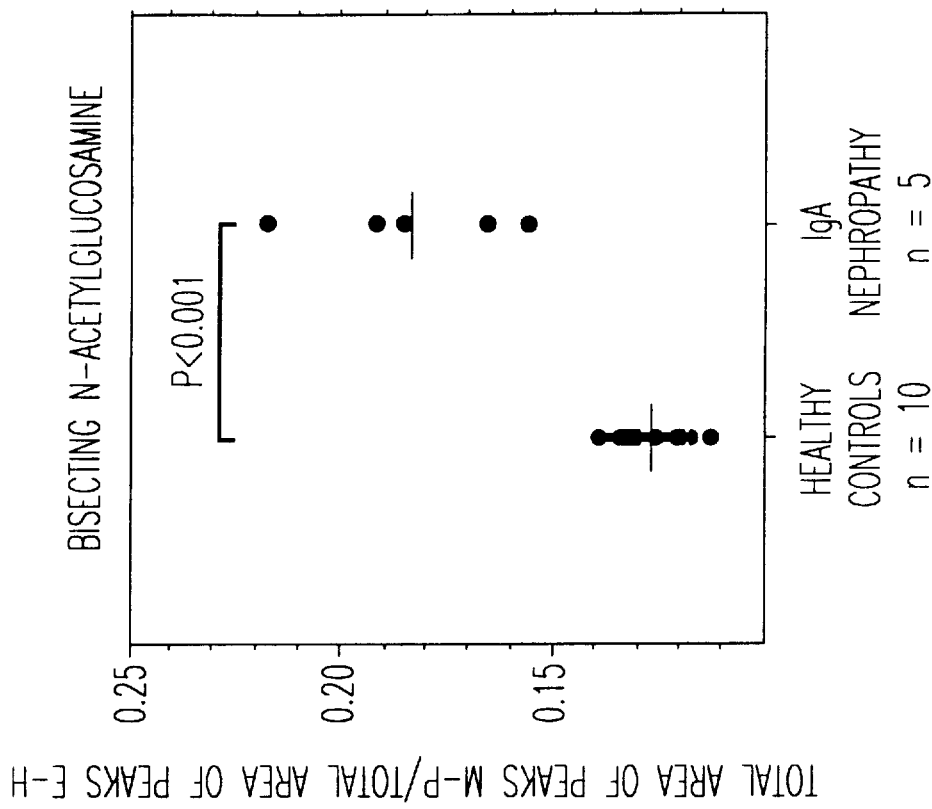
Figure 11A:
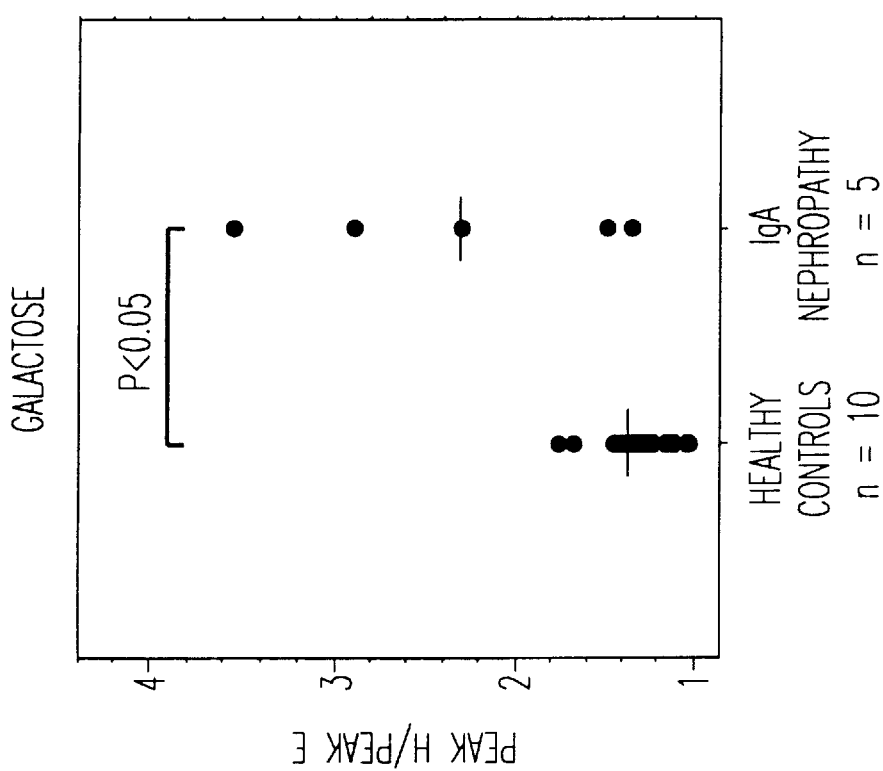

FIG. 11A shows a comparison between a group of patients with IgA nephropathy and a group of healthy controls for the alteration in the amount of galactose-containing oligosaccharides. FIG. 11B shows a comparison between a group of patients with IgA nephropathy and a group of healthy controls for the alteration in the amount of bisecting N-acetylglucosamine-containing oligosaccharides.

FIG. 12 shows elution patterns from an ODS-silica column where the samples applied were oligosaccharides of IgG from patients with neurodegenerative disorder(s) of unknown causes (FIG. 12A), Gaucher's disease (FIG. 12B), Takayasu syndrome (FIG. 12C) and Down disease syndrome (FIG. 12D), respectively.

Figures 13A, 13B, 13C:
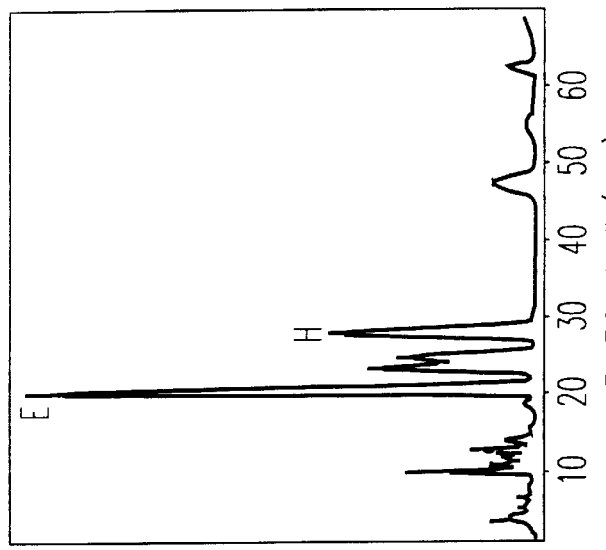

FIG. 13 shows elution patterns from an ODS-silica column where the samples applied were oligosaccharides in IgG from patients with motor dysfunction of unknown causes (FIG. 13A), multiple malformation syndrome (FIG. 13B) and Proteus syndrome (FIG. 13C), respectively.

DETAILED DESCRIPTION OF THE INVENTION

Hereinafter, the present invention is described in detail.

The method according to the present invention comprises detecting the alteration in the structures of IgG-linked oligosaccharides in collected humor such as serum in order to determine whether certain human diseases occur or not. The human diseases referred to in the present invention include but are not limited to liver disorders such as hepatitis, liver cirrhosis and hepatocellular carcinoma, malignant hypertension, IgA nephropathy and pediatric disorders. As a matter of course, the present invention can also be applied to any disease insofar as it can be examined by analysis of the alteration in the amount of bisecting N-acetylglucosamine-containing oligosaccharides or galactose-containing oligosaccharides of IgG.

As an abnormality of the structure of a sugar moiety in glycoprotein caused by human liver disease, a report is made of an abnormality in the structure of oligosaccharides in alpha fetoprotein caused by hepatocellular carcinoma. This glycoprotein is produced at an extremely low level in normal adult serum, but in serum from patients with liver diseases it is produced at a high level and kept at high concentration. In particular, it is known that serum from patients with hepatocellular carcinoma contains an increased amount of an oligosaccharide not present in serum from patients with other liver diseases such as hepatitis, liver cirrhosis, benign liver disease, etc. However, the examination of hepatocellular carcinoma by mere detection of a trace amount of alpha fetoprotein present is not sufficient and the accuracy of this examination is about 70% on hepatocellular carcinoma with a small size of about 1 cm. Hence, additional examinations such as hepatic biopsy and image diagnosis are conventionally carried out for an improvement in accuracy. However, hepatic biopsy gives pains to patients, while image diagnosis requires specific large facilities so that the number of feasible examinations is limited. Therefore, there is demand for a simple diagnosis method to easily improve accuracy in the examination of hepatocellular carcinoma.

The conventional clinical examinations of diseases are as follows:

The conventional examination of hepatitis begins with a liver function test. This test measures the activities of enzymes such as blood transaminase (sAST, sALT, etc.) and lactate dehydrogenase (LDH). The onset of hepatitis is estimated where these values are high (not less than 40 IU/l sAST, not less than 50 IU/l sALT, and not less than 500 IU/l LDH). However, even if the value returns to a normal level in the liver functional test, it is possible that hepatitis recurs due to still remaining hepatitis virus, and thus further examinations should be made in combination with other clinical methods. Inflammation as a result of hepatitis induces an abnormality of immunoreaction and then leads to an abnormality of the structures of oligosaccharides of IgG. The alteration in their structures caused by this abnormality can be examined more accurately by the method of the present invention.

The conventional diagnosis of malignant hypertension includes chemical blood examination on serum creatinine, urea nitrogen, etc., in addition to sphygmomanometry, chest x-ray, electrocardiogram and urinalysis. Malignant hypertension is a disease accompanying renal function disorders, and more than half the patients will die within one year. The methods available for the diagnosis of this disease at present are generally sphygmomanometry and retinal examination. Even if the filtration value of glomerulus in the kidney is decreased to 50%, serum creatinine and urea nitrogen to be examined in blood chemical examination often remain within a normal range, so the examination lacks in sensitivity and such items are not established as a standard indicator of malignant hypertension in the biochemical test. Because pathological IgG from patients with malignant hypertension was found to be evidently different from normal IgG in the structures of oligosaccharides of IgG, the examination of oligosaccharides of IgG can serves as the useful diagnosis of malignant hypertension in combination with the conventional examination. The present inventors found that oligosaccharides of IgG from patients with malignant hypertension have been altered because of an abnormal rise in blood pressure and that the analysis of this alteration is helpful for the early discovery of malignant hypertension.

The conventional diagnosis of IgA nephropathy is made on the basis of findings in urinalysis, serum IgA measurement and renal biopsy. In particular, urinalysis and renal biopsy are still regarded as being important although the former has disadvantages such as inconvenient collection of urine and difficult acquisition of data when stored urine is used, and the latter causes a pain and burden on patients. The present inventors have, for the first time, found the alteration of the amount of specific oligosaccharides of IgG from patients with IgA nephropathy and further they have found the correlation between the amount of the oligosaccharides with IgA nephropathy. Hence, the method of the present invention permits IgA nephrbpathy to be diagnosed in the absence of any patient's pain in combination with the conventional diagnosis method.

Unlike adult diseases, pediatric disorders include a large number of diseases, the causes of which have still not been elucidated. There are also diseases occurring exclusively in infants. However, the number of effective means that can be applied to these disorders is limited in spite of the estimation that pediatric disorders of unknown causes will increase with social diversification. The present inventors have found that a wide variety of such pediatric disorders can be grouped in terms of the alteration in the amount of oligosaccharides of pathological IgG. The present method provides a limited number of conventional examinations with a means of grouping pediatric disorders to raise diagnostic accuracy. The pediatric disorders grouped by the present method include neurodegenerative disorders, Takayasu arteritis, Down's syndrome, multiple malformation syndrome, Gaucher's disease, Proteus syndrome and motor dysfunction of unknown causes.

As diagnosis of aging, mention may be made of a study of the alteration in the amount of galactose-containing oligosaccharides of IgG (Thomas Rademacher et al., J. EXP. MED., 167, 1731–1736 (1988)). In this report, Thomas Rademacher et al. described that aging is correlated with the content of galactose in oligosaccharides and they examined the correlation of aging with the alteration in the galactose-containing oligosaccharides. In the present invention, on the other hand, there are examined various alterations such as oligosaccharides with or without galactose and oligosaccharides with or without bisecting N-acetylglucosamine of IgG. Hence, the alterations in the oligosaccharides with aging can be detected more definitely and accurately.

Urticaria is divided into allergic urticaria and non-allergic urticaria. The allergic urticaria is one kind of antigen-specific hypersensitivity induced by certain chemicals such as in pollen, foods and antibiotics. This disease is characteristic of an increase in IgE (immunogloblin normally in a trace amount in blood) together with an increase in IgG. Conventionally, this disease can be diagnosed in an allergic test by intracutaneous injection of an allergen into a patient and subsequent measurement of the resulting patch on the skin. In this method, allergic disease can be easily diagnosed, but damage to the skin often results. An alternative diagnosis involves labeling of IgE as secondary antibody with a detectable radioisotope (radioallergosorbent [RAST] test). In this test, a large amount of serum (several milliliters) is required and this method is costly and cumbersome. On the other hand, the present invention permits oligosaccharide of IgG to be analyzed with a trace amount of serum (several hundred microliters), so that the remainder of blood collected for other examination suffices in the present invention. Furthermore, the operation of the present invention can be effected safely and provide accurate data with a mechanical means in accordance with the present invention.

The examination of the complete response and non response to interferon is not established. It was reported that the therapeutic effect of interferon can be examined using its correlation with the degree of hepatic fiberization in liver histology. However, liver biopsy required in this examination will give pains to patients as described above. It was also reported that the therapeutic effect of interferon on subtypes (1a to 2b) of hepatitis virus can be examined in terms of hepatitis virus gene (RNA) previously amplified in a known method. In this examination, a less level of 1b type virus in terms of the hepatitis virus gene indicates a higher therapeutic effect of interferon, and a normal level of 2a and 2 b types virus indicates certain therapeutic effect of interferon (Murayama et al., "Rinsho Shokaki Naika", 9, 661–670 (1994)). On the other hand, the analysis in accordance with the present invention permits oligosaccharides of IgG to be effectively examined even in the absence of hepatitis virus.

The method of the present invention was completed for more accurate information on pathological changes and established as highly accurate method where there are examined not only the qualitative alteration of specific oligosaccharides of IgG in blood from patients but also their quantitative alteration by the use of a wide variety profiles of oligosaccharides of IgG.

In the present invention, oligosaccharide of IgG are purified from serum and then structurally analyzed.

As the means of identifying the structures of oligosaccharides, mention may be made of proton nuclear magnetic resonance ($^1$H-NHR) spectroscopy and mass spectrometry and high performance liquid chromatography (HPLC), among which HPLC on reverse phase chromatography column is preferably used.

Typical reverse phase chromatography makes use of an octadecyl group-bound column, octyl group-bound column, butyl group-bound column, etc. These columns can be classified according to the number of carbons bound to a carrier as the solid phase. As the octadecyl group-bound column (DS column) developed so far, mention may be made of an ODS-silica column i.e. a silica type reverse phase chromatography column with an octadecylsilyl (ODS) group bound to a carrier of silica gel and an ODP column i.e. a polymer type reverse phase chromatography column with an octadecyl group bound to a carrier of vinyl alcohol polymer. The ODS-silica column can be prepared by covalently binding an ODS group to silica gel of 5 $\mu$m diameter. Among the above reverse phase chromatography columns, the ODS-silica column enables particularly superior separation of oligosaccharides, and thus this column is preferably used in the analysis of the present invention. Commercially available ODS-silica columns, such as Nakanopak ODS-A (Nakano Vinegar Co., Ltd.), Shim-pack HRC-ODS (Shimadzu Corp., Kyoto, Japan) and Cosmosil 15$C_{18}$ (Nacalai Tesque, Inc., Kyoto, Japan) may also be used.

A wide variety of oligosaccharides can be separated in a short time by HPLC on the above-enumerated columns, and a comparison between chromatographic profiles of oligosaccharides of pathological and normal IgG provides the disease-related oligosaccharides of IgG with pathological information in clinical medicine.

The oligosaccharides are released from IgG by digestion with enzyme or chemical cleavage with anhydrous hydrazine for their examination. Although the former enzyme method is preferably used because the examination can be effected easily in the absence of a poisonous chemical substance such as anhydrous hydrazine, either method can be used without any adverse effect on analytical results. An apparatus commercially available for releasing oligosaccharides can also be used in the present invention.

Conventional labeling of the oligosaccharides includes fluorescence-labeling with 2-aminopyridine or radioisotope-labeling with tritium. Because 2-aminopyridine is easy to handle and detect in HPLC in conventional laboratories, fluorescence-labeling with 2-aminopyridine is preferably used in the present invention. As the method of fluorescence-labeling with 2-aminopyridine, mention may be made of a method of Hase et al. in which there were employed a solution of 2-aminopyridine/HCl as fluorescence-labeling agent and sodium cyanoborohydride as reducing agent (Hase et al., Biochem. Biophys. Res. Commun. 85, 257–263 (1978)) as well as a method of Kondo et al. in which there were employed a solution of 2-aminopyridine/acetic anhydride as fluorescence-labeling agent and a borane-dimethylamine complex as reducing agent (Kondo et al., Agric. Biol. Chem. 54, 2169–2170 (1990)). Either method can be used without any adverse effect on analytical results. The method of Hase et al. is advantageous in that the procedure can be effected easily with a few apparatuses. In the method of Kondo et al., an apparatus commercially available from Takara Shuzo Co., Ltd. may be employed. The fluorescence-labeled oligosaccharide is stable and analyzed advantageously by high-resolution HPLC in a short time.

The oligosaccharide fraction thus prepared is analyzed by HPLC in the following manner. First, solvent is prepared and high performance liquid chromatograph is run, and both the pump and column are equilibrated with the solvent. A mixture of standard fluorescence-labeled oligosaccharides is injected so that the conditions of the apparatus and column are confirmed, and then the sample is injected and analyzed. Proton nuclear magnetic resonance spectroscopy is carried out by high-resolution nuclear magnetic resonance unit where the spin-spin binding constant in the molecule in solution, chemical shifts, and the line width of each signal are examined. The data on the oligosaccharides in the sample are compared with those of authentic oligosaccharides so that their structures can be identified. In mass spectroscopy, the sample is ionized under vacuum by electron bombardment and ions are separated according to their mass number/charge, and their mass spectral fragmentation pattern is examined.

Hereinafter, the method of the present invention is described in brief.

The blood collected from an examinee is applied to a Protein G column (Pharmacia Biotech). From the column, the IgG is eluted, concentrated, dissolved in 0.01N HCl (pH 2) and heated for the removal of sialic acid. The sample is digested with protease and then glycoamidase A to release oligosaccharides. The oligosaccharides are desalted and purified on cation and anionic exchange resins respectively and then fluorescence-labeled with 2-aminopyridine. The oligosaccharides are further purified through a Sephadex G-15 column. The sample thus obtained is then analyzed by HPLC in accordance with the present invention.

The present invention provides highly accurate information in a manner applicable to practical operation for examination of diseases such as liver diseases, allergic diseases, malignant hypertension, IgA nephropathy and pediatric disorders, as well as aging-depending variations and the therapeutic effect of interferon. Furthermore, the method of the present invention can attain higher accuracy in combination with other examinations and is extremely useful as a clinical examination method.

EXAMPLES

The present invention is described in more detail with reference to the following examples, which however are not intended to limit the scope of the invention.

Example 1

The oligosaccharides of IgG were purified from human serum to analyze the alteration in the amount of bisecting N-acetylglucosamine-containing oligosaccharides in HPLC.

Preparation

For the preparation of IgG, 250 $\mu$l human serum was applied to Protein G column (a product of Pharmacia Biotech) and eluted with buffer A (20 mM sodium phosphate, pH 7) and buffer B (50 mM acetic acid, pH 3) to give about 3.3 mg IgG, and the eluent was concentrated.

The concentrated IgG was dissolved in 0.01N HCl (pH 2), adjusted to pH 2, and heated at 90° C. for 1 hour for removal of sialic acid linked at a non-reducing terminal of the oligosaccharide, and then digested enzymatically with pepsin. The reaction solution was adjusted within the range of pH 4 to 6, and oligosaccharides were released with an enzyme, glycoamidase A. The sample was centrifuged for removal of solids. The supernatant was desalted through cation-exchange and anion-exchange resins equilibrated with deionized water, respectively.

100 $\mu$l reaction reagent (2-aminopyridine/HCl, pH 6.8) was added to 100 nmol of the dried oligosaccharides and heated at 100° C. for 20 min. A reducing agent solution was added thereto and allowed to react at 90° C. for 12 hours.

The oligosaccharides were purified through a Sephadex G-15 column. The 2-aminopiridine-oligosaccharide fraction was collected, dried and analyzed by HPLC.

Analysis conditions in HPLC
* Solvent A: 10 mM sodium dihydrogen phosphate, pH 3.8.
* Solvent B: solvent A plus 0.5% n-butanol.
* Fluorometric detector: Shimadzu RF-550 (Shimadzu Corp., Kyoto, Japan).
* Detection: fluorescence detection (excitation wavelength: 320 nm, emission wavelength: 400 nm).
* Flow rate: 1 ml/min.
* Column temperature: 55° C.
* Elution of oligosaccharides: After injection, the proportion of solvent B was increased linearly from 20% to 50% in 60 min.

Results

The oligosaccharide samples used were prepared from human serum-derived IgG from 8 healthy controls and 21 patients with liver diseases (8 patients with hepatitis, 6 patients with liver cirrhosis and 7 patients with hepatocellular carcinoma). FIG. 1 shows an elution pattern obtained in HPLC under the above-described conditions. This elution profile reflects the structural versatility among the slightly different affinities of the IgG oligosaccharides for the ODS silica column. As mentioned above, the ratio of the amounts of oligosaccharides of normal IgG is constant. Hence, the following ratio was determined for evaluation of the alteration in the amount of bisecting N-acetylglucosamine-containing oligosaccharides.

Alteration in the amount of bisecting N-acetylglucosamine-containing oligosaccharides=the ratio in the total area of peaks E, F, G and H (group II) to that of peaks M, N, O and P (group IV).

Figure 2:
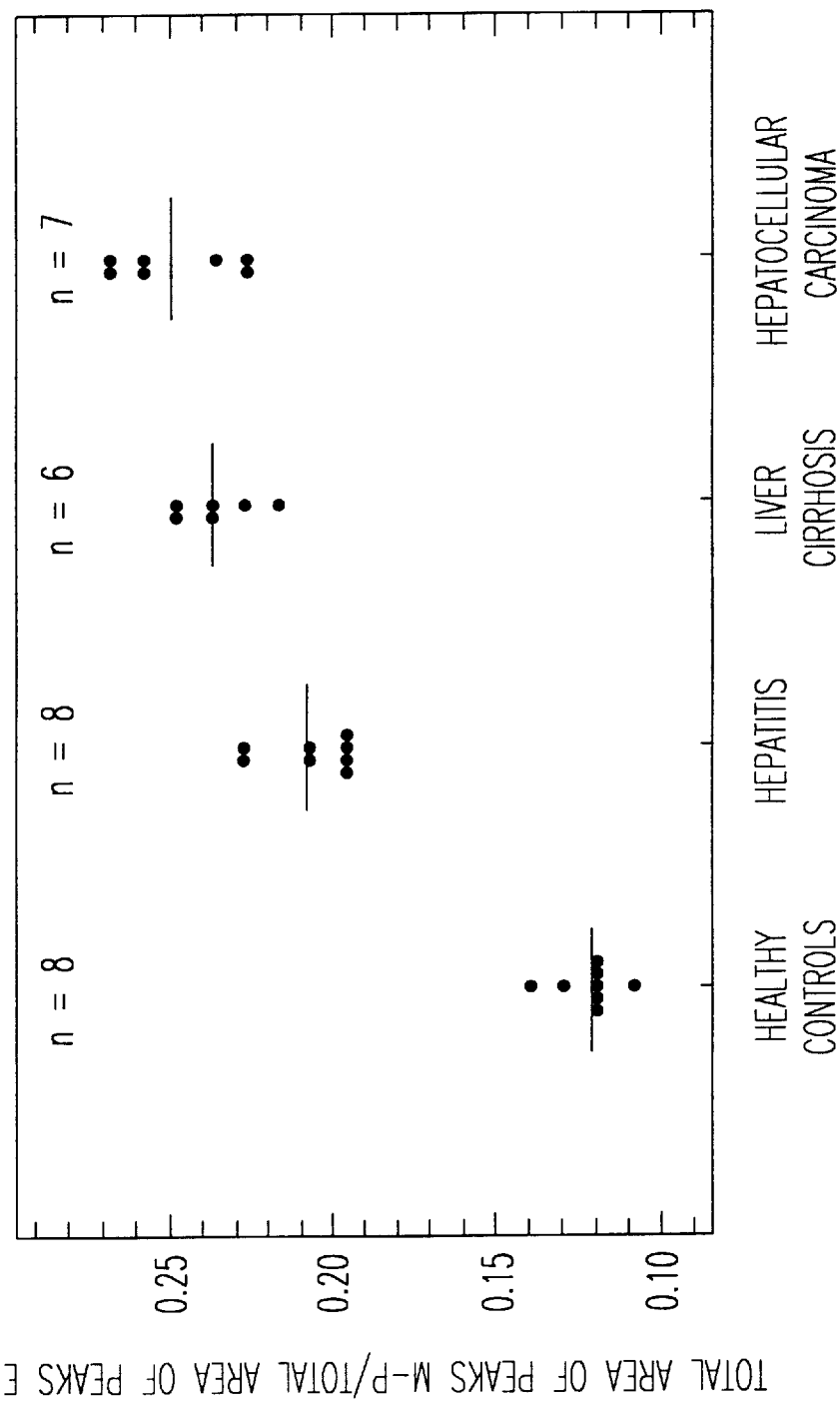
FIG. 2 shows the amounts of bisecting N-acethylglucosamine-containing oligosaccharides of IgG from the healthy controls and patients (hepatitis, liver cirrhosis and hepatocellular carcinoma).

As shown in FIG. 2, the difference in the amounts of the bisecting N-acetylglucosamine-containing oligosaccharides from the healthy controls and the patients with hepatitis was statistically significant ($p<0.001$). Out of the elution peaks A–P from the ODS-silica column, the peaks M–P/peaks E–H ratio is indicated on the ordinate, and healthy controls and patients with each liver disease are indicated on the abscissa in FIG. 2. "n" is the total number of examinees and one examinee is indicated as a dot with the corresponding ratio. As shown in FIG. 2, the amount of the bisecting N-acetylglucosamine-containing oligosaccharides of pathological IgG is higher than that of normal IgG. Hence, the analysis of oligosaccharides of IgG provides useful information for the diagnosis of hepatitis.

Example 2

To examine the alteration in the amount of galactose-containing oligosaccharides of IgG, oligosaccharides of human IgG from healthy controls and patients with hepatitis were analyzed in the same manner as in Example 1. The samples used were the same as in Example 1.

The following ratio was determined for evaluation of the alteration in the amount of galactose-containing oligosaccharides: Alteration in galactose=the ratio of the total area of peaks E–M to that of galactose-containing oligosaccharide peaks (that is, $[E+M]/[F+G+2H+N+O+2P]$. As shown in this equation, the area of each of peaks H and P was multiplied by 2 because 2 galactose molecules exist in the oligosaccharide of each of peaks H and P.).

Figure 3:
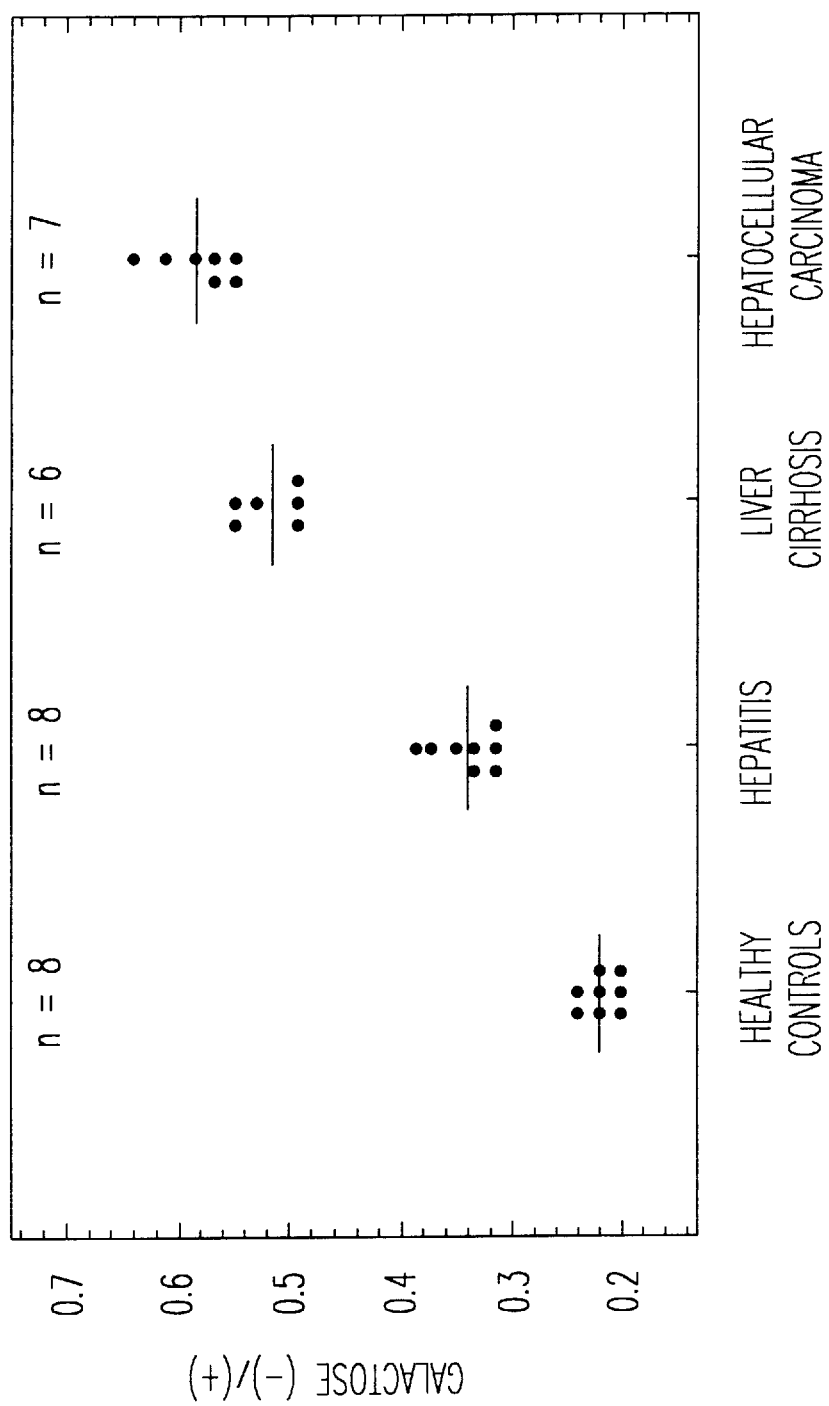
FIG. 3 shows the amounts of galactose-containing oligosaccharides of IgG from the healthy controls and patients (hepatitis, liver cirrhosis and hepatocellular carcinoma).

The alterations in the amounts of galactose-containing oligosaccharides of each IgG is shown in FIG. 3 where the ratio of peaks E–M to the galactose-containing peaks (galactose (–)/galactose (+)) is indicated on the ordinate and the healthy controls and patients with each liver disease are indicated on the abscissa. "n" is the total number of examinees, and one examinee is shown as a dot with the corresponding ratio. The difference between the healthy controls and the patients with hepatitis was statistically significant ($p<0.05$). Further, there was a significant difference between the patients with liver cirrhosis and those with liver cirrhosis and hepatocellular carcinoma ($p<0.001$). The above results indicated that a lower amount of galactose-containing oligosaccharides is contained in each pathological IgG than normal IgG. Hence, the analysis of oligosaccharides of IgG provides useful information for diagnosis of patients with liver diseases.

Example 3

The oligosaccharides of IgG from patients with an allergic disease were analyzed in the same manner as in Example 1.

In this example, 6 healthy controls and 2 patients with neurourticaria caused by fatigue were examined.

FIGS. 4A and 4B show the elution patterns in HPLC. A comparison between the two chromatographic profiles reveals that peak F is smaller with respect to the area than peak G in normal IgG, as opposed to pathological IgG where peak F is larger than peak G and this elution pattern of peaks F and G is characteristic of oligosaccharides of IgG from patients with an allergic disease. Hence, the analysis of oligosaccharides of IgG provides useful information for diagnosis of patients with an allergic disease.

Example 4

To evaluate the effect of interferon, IgG from patients with chronic C-type hepatitis was examined in the same manner as in Example 1.

For this example, interferon was administrated into patients with chronic C-type hepatitis, and before and after this administration, serum was collected from 3 patients with the complete response to interferon and 4 patients with non response. For analysis of the oligosaccharides, IgG was purified from each serum.

Figure 6B:
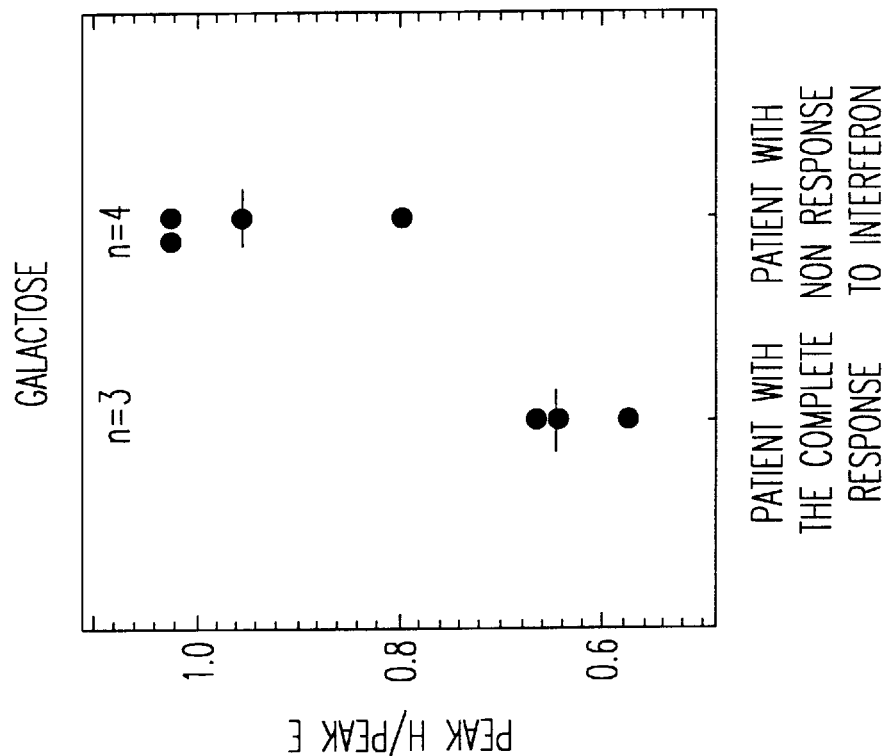
FIG. 6 shows the alterations between patients with the complete response to interferon and those with non response in the amounts of bisecting N-acetylglucosamine (FIG. 6A) and galactose (FIG. 6B) containing oligosaccharides, respectively.
Figure 6A:
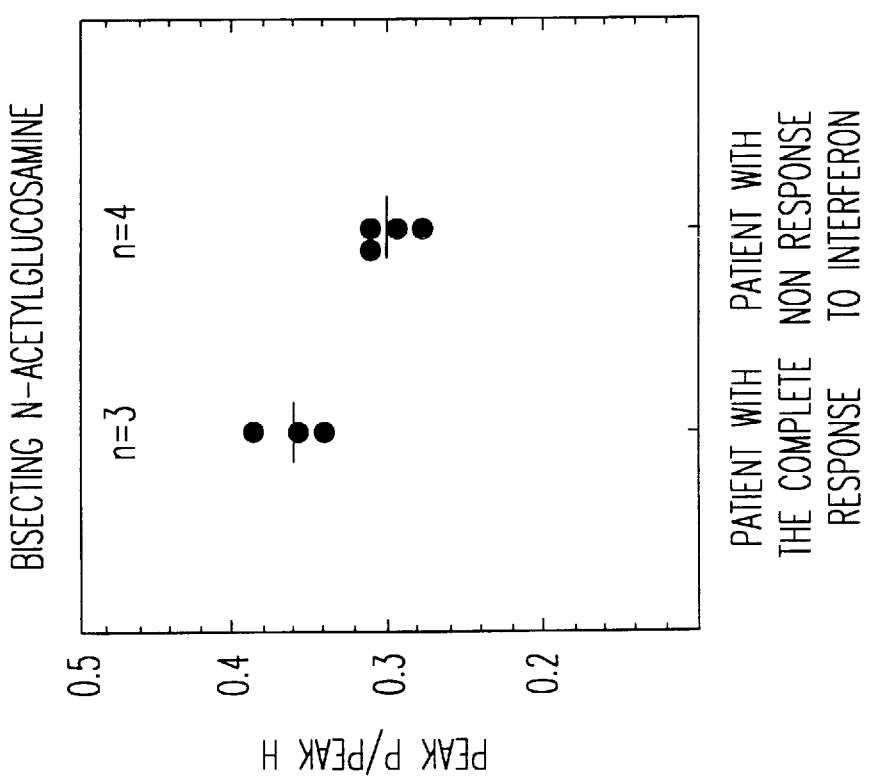

FIGS. 5A and 5B show an elution pattern in HPLC of each of the samples from patients with the complete response to interferon and non response. FIGS. 6A and 6B show the alterations in the amounts of bisecting N-acetylglucosamine-containing oligosaccharides and galactose-containing oligosaccharides, respectively.

The following ratios were determined for evaluation of the alterations in the amounts of bisecting N-acetylglucosamine-containing oligosaccharides and galactose-containing oligosaccharides.

Alteration in bisecting N-acetylglucosamine-containing oligosaccharides=peak P/peak H.

Alteration in galactose-containing oligosaccharides=peak H/peak E. "n" is the number of examinees.

The results indicated that a larger amount of bisecting N-acetylglucosamine-containing oligosaccharides and a less amount of galactose-free oligosaccharides were contained in IgG from patients with the complete response to interferon than in IgG from patients with non response, and their difference was statistically significant. Hence, the analysis of oligosaccharides of IgG provides useful information for evaluation of the effect of interferon.

Example 5

The alteration in oligosaccharides of IgG as an indicator of aging was examined in the same manner as in Example 1.

FIG. 7 shows the analytical results of oligosaccharides of IgG from 8 normal serum. The following ratios were determined for evaluation of the amounts of oligosaccharides of IgG.

Alteration in the amount of the bisecting N-acetylglucosamine-containing oligosaccharides=(M+N+O+P)/(E+F+G+H).

Alteration in the amount of galactose-containing oligosaccharides=H/E.

Figure 7B:
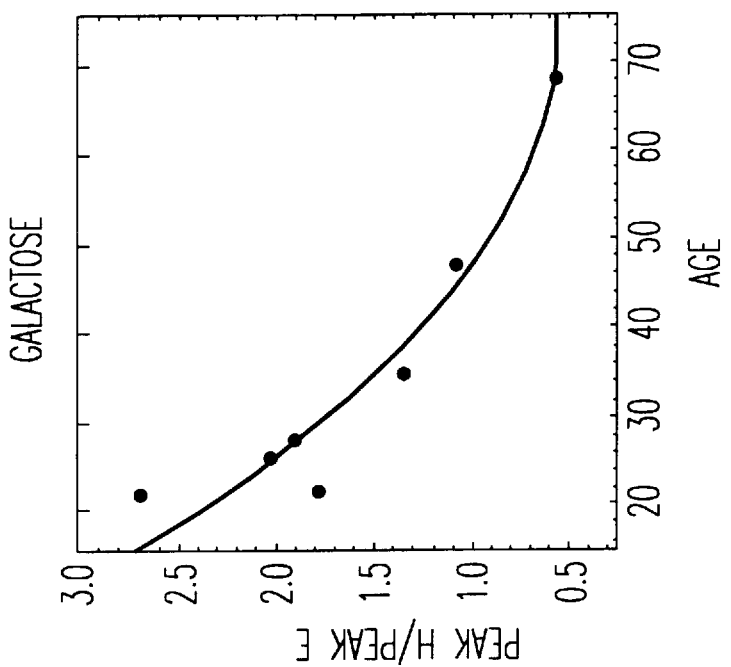
FIGS. 7A and 7B show the alterations with aging in the amounts of bisecting N-acetylglucosamine-containing oligosaccharides and galactose-containing oligosaccharides, respectively.
Figure 7A:
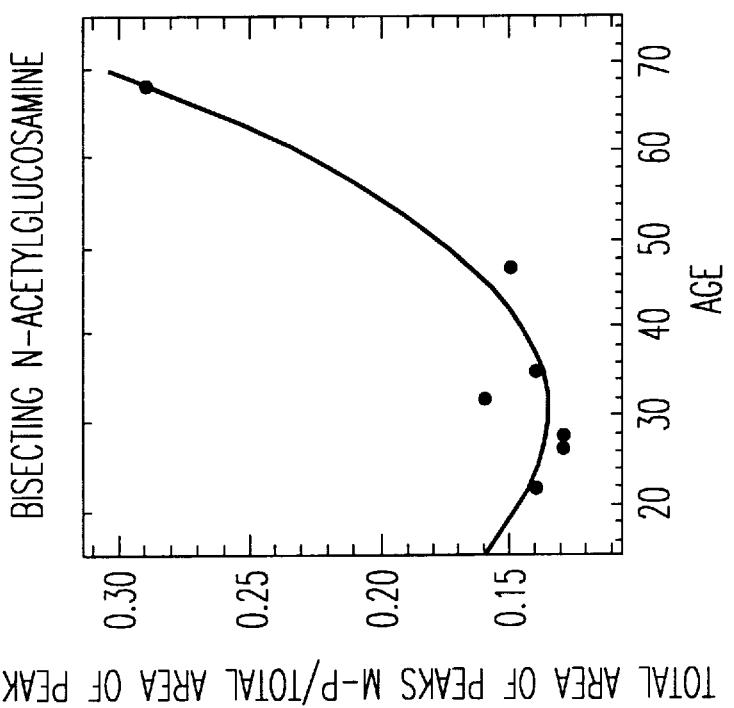

FIGS. 7A and 7B show the results along with their curvilinear regression. The respective curves are as follows:
FIG. 7A:
Total area of peaks M–P/total area of peaks E–H=$1.07 \times 10^{-4}$ (age)$^2$–$6.45 \times 10^{-3}$ (age)+0.23. Multiple correlation coefficient: 0.976.
FIG. 7B:
Peak H/peak E=$6.56 \times 10^{-4}$ (age)$^2$–0.10 (age)+4.03. Multiple correlation coefficient: 0.923.

The amount of bisecting N-acetylglucosamine-containing oligosaccharides (M+N+O+P/E+F+G+H) increases with aging, while the amount of galactose-containing oligosaccharides (H/E) decreases with aging. This indicates an alteration with aging in the structures of the oligosaccharides, and their analysis provides useful information for evaluation of aging as well as preventive diagnosis of disease.

Example 6

The oligosaccharides of IgG from 3 patients with malignant hypertension were analyzed in the same manner as in Example 1 except that two kinds of HPLC columns (ODS column and ODS-silica column) were used.

Analysis conditions in HPLC
* Solvent A: 10 mM sodium dihydrogen phosphate, pH 3.8.
* Solvent B: solvent A plus 0.5% n-butanol.
* Fluorometric detector: Shimadzu RF-550 (Shimadzu Corp., Kyoto, Japan).
* Detection: fluorometric detection (excitation wavelength: 320 nm, emission wavelength: 400 nm).
* Flow rate: 1 ml/min.
* Column temperature: 55° C.
* Elution conditions of oligosaccharides:

ODP column . . . After the sample was injected, the proportion of solvent B was increased linearly from 0% to 15% in 60 min.

ODS-silica column . . . After the sample was injected, the proportion of solvent B was increased linearly from 20% to 50% in 60 min.
* Columns:

ODR column . . . Asahipak ODS-50 (4.6$\phi$×150 mm) (Asahi Chemical Industry Co., Ltd.).

ODS-silica column . . . Nakanopak-ODS (6.0$\phi$×150 mm) (Nakano Vinegar Co., Ltd.).
Results The results are shown in FIGS. 8A–8D. A comparison between FIGS. 8A–8D indicates that both the columns show a clear difference in oligosaccharides between normal IgG and pathological IgG and thus prove useful in this examination.

As is evident from FIGS. 8B and 8D, peak E is smaller than peak H in normal IgG, whereas, in pathological IgG, peak E is larger than peak H and the ratio of bisecting N-acethylglucosamine-containing oligosaccharides to the other oligosaccharides is raised. In addition, the pathological IgG shows the tendency of increasing areas of the main peaks (peaks E, F, G and H) and decreasing areas of the bisecting N-acetylglucosamine-containing oligosaccharides (peaks M, N, O and P) with elution volume, respectively. This pattern of the peaks is characteristics of oligosaccharides of IgG from patients with malignant hypertension. The alterations in galactose-containing oligosaccharides and bisecting N-acetylglucosamine-containing oligosaccharides are two-dimensionally shown in FIG. 9. The following ratios were determined.

Alteration in the amount of galactose-containing oligosaccharides=peak H/peak E.

Alteration in the amount of bisecting N-acetylglucosamine-containing oligosaccharides=peaks M–P/peaks E–H.

Figure 9:
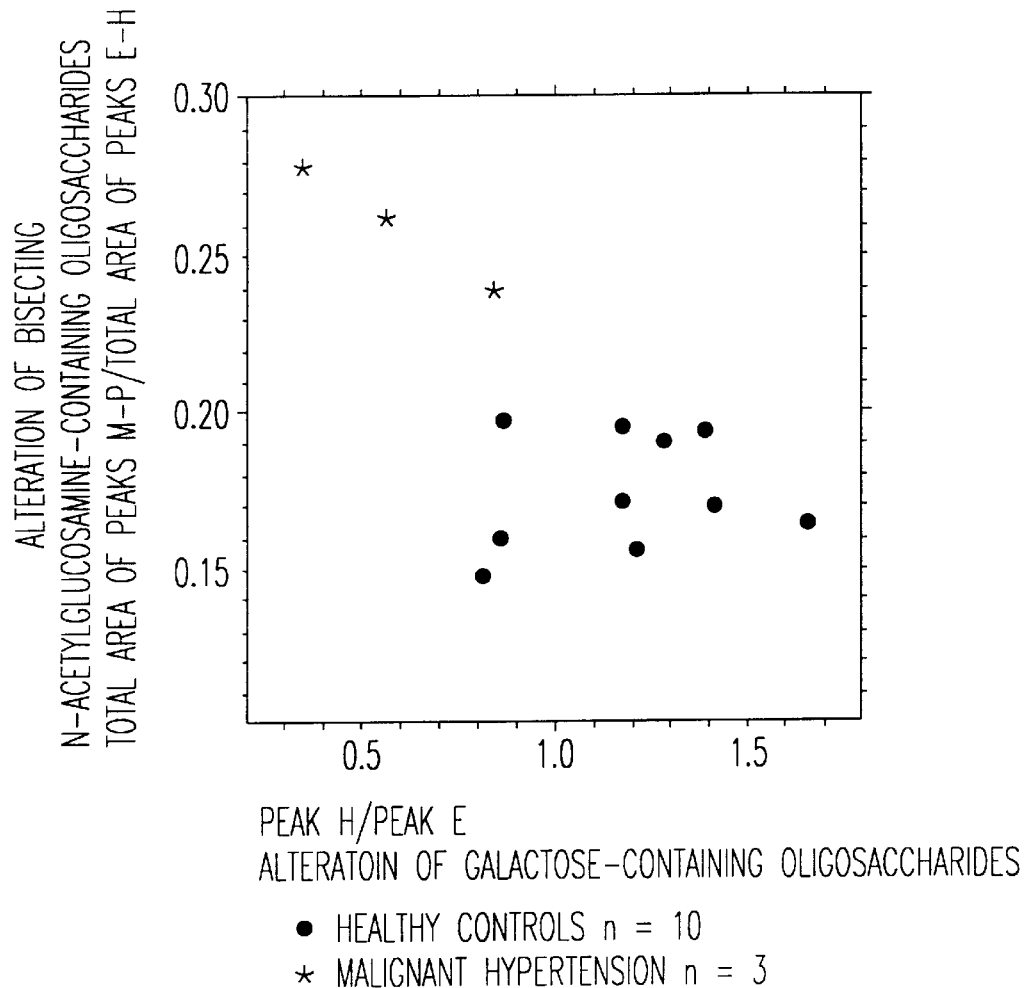
FIG. 9 shows the alterations in the amounts of galactose-containing oligosaccharides on the abscissa and bisecting N-acetylglucosamine-containing oligosaccharides on the ordinate, where the sample used was derived from IgG from patients with malignant hypertension. The alterations in their amounts were determined as follows.

As shown in FIG. 9, the normal IgG and pathological IgG can be clearly distinguished on the basis of both the alterations in galactose-containing oligosaccharides and bisecting N-acetylglucosamine-containing oligosaccharides. Hence, the examination of oligosaccharides of IgG provides an indicator of malignant hypertension.

Example 7

The oligosaccharides of IgG from 5 patients with IgA nephropathy were examined in the same manner as in Example 1.

FIG. 10 shows an elution pattern on IgA nephropathy in HPLC. FIGS. 11A and 11B show the alterations in galactose-containing oligosaccharides and bisecting N-acetylglucosamine-containing oligosaccharides, respectively. These alterations were determined in the same manner as in Example 6. The peak H/peak E ratio is indicated on the ordinate and the healthy controls and patients with IgA nephropathy are indicated on the abscissa. "n" is the total number of examinees, and one examinee is shown as a dot with the corresponding peak H/peak E ratio.

The result indicated that a larger amount of galactose-containing oligosaccharides exists in the patients with IgA nephropathy than in the healthy controls, and the difference therebetween was statistically significant (p<0.05). Then, the alteration in the amount of bisecting N-acetylglucosamine-containing oligosaccharides was examined. The ratio (total area of peaks M–P/total area of peaks E–H) is indicated on the ordinate and the healthy controls and patients with IgA nephropathy are indicated on the abscissa. One examinee is indicated as a dot with the corresponding ratio of peaks M–P/peaks E–H.

According to the results, the difference between the normal IgG and pathological IgG was statistically significant (p<0.001). Hence, the analysis of oligosaccharides of IgG provides useful information for diagnosis of patients with IgA nephropathy.

Example 8

The oligosaccharides of IgG from infants with the following typical pediatric disorders diagnosed by a pediatrician were examined in the same manner as in Example 1.

The diseases examined are: development delay; multiple malformation syndrome; hyperammonemia; mental retardation; neurodegenerative disorders; homocystinuria; growth hormone deficiency; Gaucher's disease; Prader-Willi syndrome; Wilson's disease; mucopolysaccharidoses; phenylketonuria; Proteus syndrome; cystinosis; Aicardi syndrome; fat malabsorption; renal dysgenesis; cerebellar hypoplasia; glycogen storage disease; motor dysfunction of unknown causes; autism; nephropathy associated with liver cirrhosis; Down's syndrome; maple syrup urine disease; focal glomerular scleroses; Takayasu arteritis; and the progressive encephalopathy syndrome with edema, hyparrhythmia and optic atrophy syndrome (the PEHO syndrome).

FIGS. 12 and 13 show elution patterns in HPLC on oligosaccharides in IgG from patients with neurodegenerative disorders, Takayasu arteritis, Down's syndrome, multiple malformation syndrome, Gaucher's disease, Proteus syndrome and motor dysfunction of unknown causes, which differ from the elution pattern profile on the healthy controls in FIG. 4A. In contract to this profile of normal IgG, FIGS. 12 and 13 reveal that peak E is larger than peak H in every pathological IgG, indicating that the amount of galactose-free oligosaccharides is higher than galactose-containing oligosaccharides in every case.

The amount of galactose-containing oligosaccharides in each chromatogram was used for a comparison between healthy controls (10 persons) and patients with neurodegenerative disorders, Takayasu arteritis, Proteus syndrome, Gaucher's disease and motor dysfunction of unknown causes. The results are shown in Table 1. Further, the amount of bisecting N-acetylglucosamine-containing oligosaccharides in each chromatogram was used for a comparison between the healthy controls and patients with Down's syndrome, multiple malformation syndrome and Takayasu arteritis. The results are shown in Table 2. The following ratio was determined for the evaluation of the amounts. Alteration in the amount of galactose-containing oligosaccharides=ratio of the total area of peaks E and M to the total area of the galactose-containing peaks (galactose (−)/galactose (+)). Alteration in the amount of bisecting N-acetylglucosamine-containing oligosaccharides=total area of peaks M–P/total area of peaks E–H.

TABLE 1

|  | galactose (−)/(+) |
|---|---|
| normal controls n = 10 | 0.231 ± 0.032 |
| neurodegenerative disease | 0.548 |
| Takayasu arteritis | 0.452 |
| Proteus syndrome | 0.597 |
| Gaucher's disease | 0.753 |
| motor dysfunction of unknown causes | 0.475 |

TABLE 2

|  | total area of peaks M-P/total area of peaks E-H |
|---|---|
| normal controls n = 10 | 0.128 ± 0.009 |
| Down's syndrome | 0.218 |
| multiple malformation syndrome | 0.234 |
| Takayasu arteritis | 0.189 |

Pathological IgG from patients with the above diseases showed a clear difference from normal IgG in terms of two factors, i.e. alterations in the amounts of galactose-containing oligosaccharides and bisecting N-acetylglucosamine-containing oligosaccharides. Hence, the use of the two factors provides a screening examination for pediatric disorders to which a limited number of examination methods can be applied.

What is claimed is:

1. A method for examination of a human disease selected from the group consisting of liver diseases, malignant hypertension, immunoglobin A nephropathy and pediatric disorders, which comprises analyzing an alteration in the amount ratio of bisecting N-acetylglucosamine-containing oligosaccharides to bisecting N-acetylglucosamine-free oligosaccharides of immunoglobin G oligosaccharides in a collected humor as compared to the corresponding amount ratio in normal humans.

2. A method for examination of a human disease according to claim 1, which comprises purifying immunoglobin G from a collected humor, separating oligosaccharides from the purified immunoglobin G, labeling the separated oligosaccharides and subjecting the labeled oligosaccharides to high performance liquid chromatography on a reversed phase chromatography column to analyze an alternation in the amount ratio of bisecting N-acetylglucosamine-containing oligosaccharides to bisecting N-acetylglucosamine-free oligosaccharides of immunoglobin G oligosaccharides in the collected humor based on the elution pattern.

3. A method for examination of a human disease according to claim 1, wherein pediatric disorders are selected from the group consisting of development delay; multiple malformation syndrome; hyperammonemia; mental retardation; neurodegenerative disorders; homocystinuria; growth hormone deficiency; Gaucher's disease; Prader-Willi syndrome; Wilson's disease; mucopolysaccharidoses; phenylketonuria; Proteus syndrome; cystinosis; Aicardi syndrome; fat malabsorption; renal dysgenesis; cerebellar hypoplasia; glycogen storage disease; motor dysfunction of unknown causes; autism; nephropathy associated with liver cirrhosis; Down's syndrome; maple syrup urine disease; focal glomerular scleroses; Takayasu arteritis; and the progressive encephalopathy syndrome with edema, hyparrhythmia and optic atrophy syndrome (the PEHO syndrome).

4. A method for examination of a human disease selected from the group consisting of liver diseases, malignant hypertension, immunoglobin A nephropathy and pediatric disorders, which comprises analyzing alteration in the amount ratio of N-acetylglucosamine-containing oligosaccharides to N-acetylglucosamine-free oligosaccharides and/or the amount ratio of galactose-containing oligosaccharides to galactose-free oligosaccharides of immunoglobin G oligosaccharides in a collected humor as compared to the corresponding amount ratio in normal humans, wherein said pediatric disorders are selected from the group consisting of development delay; multiple malformation syndrome; hyperammonemia; mental retardation; neurodegenerative disorders; homocystinuria; growth hormone deficiency; Gaucher's disease; Prader-Willi syndrome; Wilson's disease; mucopolysaccharidoses; phenylketonuria; Proteus syndrome; cystinosis; Aicardi syndrome; fat malabsorption; renal dysgenesis; cerebellar hypoplasia; glycogen storage disease; motor dysfunction of unknown causes; autism; nephropathy associated with liver cirrhosis; Down's syndrome; maple syrup urine disease; focal glomerular scleroses; Takayasu arteritis; and the progressive encephalopathy syndrome with edema, hyparrhythmia and optic atrophy syndrome (the PEHO syndrome).

5. A method for examination of a human disease according to claim 4, which comprises purifying immunoglobin G from a collected humor, separating oligosaccharides from the purified immunoglobin G, labeling the separated oligosaccharides and subjecting the labeled oligosaccharides to high performance liquid chromatography on a reversed phase chromatography column to analyze an alteration in the amount ratio of bisecting N-acetylglucosamine-containing oligosaccharides to bisecting N-acetylglucosamine-free oligosaccharides and/or in the amount ratio of galactose-containing oligosaccharides to galactose-free oligosaccharides of immunoglobin G oligosaccharides in the collected humor based on the elution pattern.

6. A method for examination of a human disease according to claim 2 or 5, in which the reversed chromatography column is an octadecylsilyl (ODS) silica column.

* * * * *

UNITED STATES PATENT AND TRADEMARK OFFICE
CERTIFICATE OF CORRECTION

PATENT NO. : 5,831,037
DATED: : November 3, 1998
INVENTOR(S) : Hiroyuki OHSUGA et al It is certified that error appears in the above-identified patent and that said Letters patent is hereby corrected as shown below:

In the Title Page [54], delete "METHOD FOR CLINICAL EXAMINATION BASED ON THE STRUCTURES OF IMMUNOGLOBIN G-LINKED OLIGOSACCHARIDES" and replace with-- METHOD FOR CLINICAL EXAMINATION BASED ON THE STRUCTURES OF IMMUNOGLOBLIN G-LINKED OLIGOSACCHARIDES--

Col. 1, line 3, "IMMUNOGLOBIN" should read --IMMUNOGLOBLIN--.

Signed and Sealed this

Twenty-fifth Day of May, 1999

*Attest:*

Q. TODD DICKINSON

*Attesting Officer*     *Acting Commissioner of Patents and Trademarks*

UNITED STATES PATENT AND TRADEMARK OFFICE
CERTIFICATE OF CORRECTION

PATENT NO. : 5,831,037
DATED : November 3, 1998
INVENTOR(S) : Hiroyuki Ohsuga, et al.

It is certified that error appears in the above-indentified patent and that said Letters Patent is hereby corrected as shown below:

Column 15, Line 58 "immunoglobin" should read --immunogloblin--.

Column 15, Line 62 "immunoglobin" should read --immunogloblin--.

Column 15, Line 66 "immunoglobin" should read --immunogloblin--.

Column 16, Line 2 "immunoglobin" should read --immunogloblin--.

Column 16, Line 8 "immunoglobin" should read --immunogloblin--.

Column 16, Line 28 "immunoglobin" should read --immunogloblin--.

Column 16, Line 33 "immunoglobin" should read --immunogloblin--.

Column 16, Line 50 "immunoglobin" should read --immunogloblin--.

UNITED STATES PATENT AND TRADEMARK OFFICE
CERTIFICATE OF CORRECTION

PATENT NO. : 5,831,037
DATED : November 3, 1998
INVENTOR(S) : Hiroyuki Ohsuga, et al.

It is certified that error appears in the above-indentified patent and that said Letters Patent is hereby corrected as shown below:

Column 16, Line 52 "immunoglobin" should read --immunogloblin--.

Column 16, Line 60 "immunoglobin" should read --immunogloblin--.

Signed and Sealed this

Twelfth Day of October, 1999

Q. TODD DICKINSON

*Attest:*

*Attesting Officer*         Acting Commissioner of Patents and Trademarks